United States Patent [19]

Moore

[11] Plant 5,174

[45] Jan. 10, 1984

[54] GRAPEVINE—RELIANCE CULTIVAR

[75] Inventor: James N. Moore, Fayetteville, Ark.

[73] Assignee: Arkansas Agricultural Experiment Station, University of Arkansas, Fayetteville, Ark.

[21] Appl. No.: 438,403

[22] Filed: Dec. 27, 1982

[51] Int. Cl.[3] ..... A01H 5/03

[52] U.S. Cl. ..... Plt./47

[58] Field of Search ..... Plt./47

*Primary Examiner*—Robert E. Bagwill

[57] ABSTRACT

Description and specifications of a new and distinct grapevine variety which originated from seed produced by a hand-pollinated cross of Ontario (non-patented) and Suffolk Red (non-patented) is provided. This new grapevine variety can be distinguished by its early maturing seedless fruit of attractive red color and unique flavor, and by its outstanding cold hardiness to low midwinter temperatures.

2 Drawing Figures

SUMMARY OF THE INVENTION

The new and distinct variety of grapevine originated from a hand pollinated cross of Ontario (non-patented)-×Suffolk Red (non-patented), made in 1964 at the University of Arkansas experimental vineyard at Clarksville, Ark. The seeds resulting from this controlled hybridization were germinated in a greenhouse during the winter of 1964–65. Resulting seedlings were planted in the spring of 1965 in a field on the Arkansas Agricultural Experiment Station at Clarksville, Ark. The seedlings fruited during the summer of 1967 and one, designated Ark. 1163, was selected for its outstanding flavor, attractive color, and seedless fruit.

During 1968, the selection was propagated asexually by rooting hardwood cuttings and a first test planting of four vines was established. Subsequently larger test plantings have been established with asexually multiplied vines at four additional locations in Arkansas and on state agricultural experiment stations in Ohio, Texas, Wisconsin and North Carolina.

The new variety has been asexually multiplied annually since 1968 by the rooting of both hardwood and softwood cuttings and by grafting onto rootstocks. It roots readily from both hardwood and softwood cuttings and no graft incompatibility has been observed. During all asexual multiplication, the characteristics of the original plant have been maintained.

Test plantings over a wide geographic area have shown this new variety to be widely adapted to differing climatic and soil conditions. It has performed well from the warm climate of southwest Texas to the cold winter areas of Wisconsin and Ohio. The plants are very winter-hardy, having survived and fruited for eight consecutive years at Sturgeon Bay, Wis. during which time temperatures have reached −34° C. It has also demonstrated above average cold hardiness in Ohio tests.

Vines of the new variety are vigorous and typically labrusca in character. It has produced well as own-rooted plants in all locations tested except on the high pH, calcareous soils of southwest Texas, where it must be grafted. The vines are moderately resistant to black rot {*Guignardia bidwellii* (Ell.) V. & R.}, anthracnose {*Elsinoe ampelina* (d. By.) Shear}, powdery mildew (*Uncinula necator* Burr.) and downy mildew (*Plasmopora viticola* Berl. & Tomi.). A spray program that will control these diseases on the Concord variety is sufficient for control on the new variety.

Fruit of the new variety ripens early, about with the Fredonia cultivar. Average ripening date is July 25 in central Arkansas, August 24 at Wooster, Ohio and September 10 at Sturgeon Bay, Wis. Good color development does not occur until the fruit is fully mature, but fruit is sweet and well-flavored at the color inception stage. In cold storage tests, fruit has kept well for about three months.

The fruit is round in shape and pink in color at maturity. Berries are medium in size (ca. 2.7 g). The fruit is of the stenospermocarpic type of seedlessness and contains very small vestigial seed traces that are not noticeable when eaten. Skins of the fruit are very tender and the flesh is melting in texture. Soluble solids are very high, and combines with a delicate labrusca aroma and flavor, produce a sweet, pleasing taste that is rated as unique and outstanding. Clusters are medium-large (ca. 300 g), cylindrical and well filled, but not excessively compact. In Arkansas and North Carolina, fruit has shown a tendency to crack in some years following rains during the final maturation period, but this condition has not been observed in Ohio, Wisconsin or Texas.

The new variety has been named the 'Reliance' cultivar.

BRIEF DESCRIPTION OF THE PHOTOGRAPHS

The accompanying photographs show typical specimens of the fruit and leaves of the new variety in color as nearly true as it is reasonably possible to make in a color illustration of this character.

DETAILED DESCRIPTION OF THE NEW VARIETY

Figure 1:
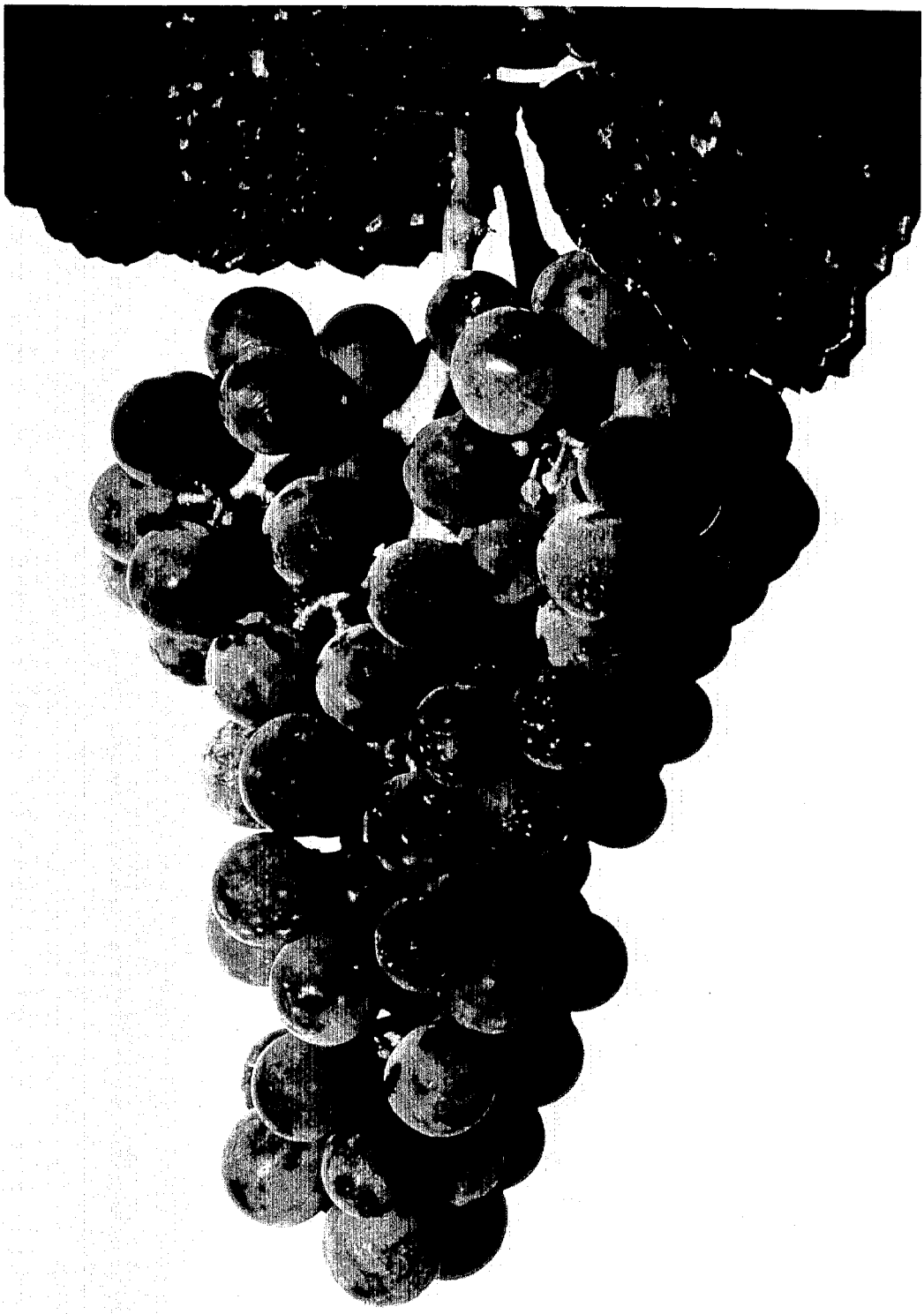
Figure 2:
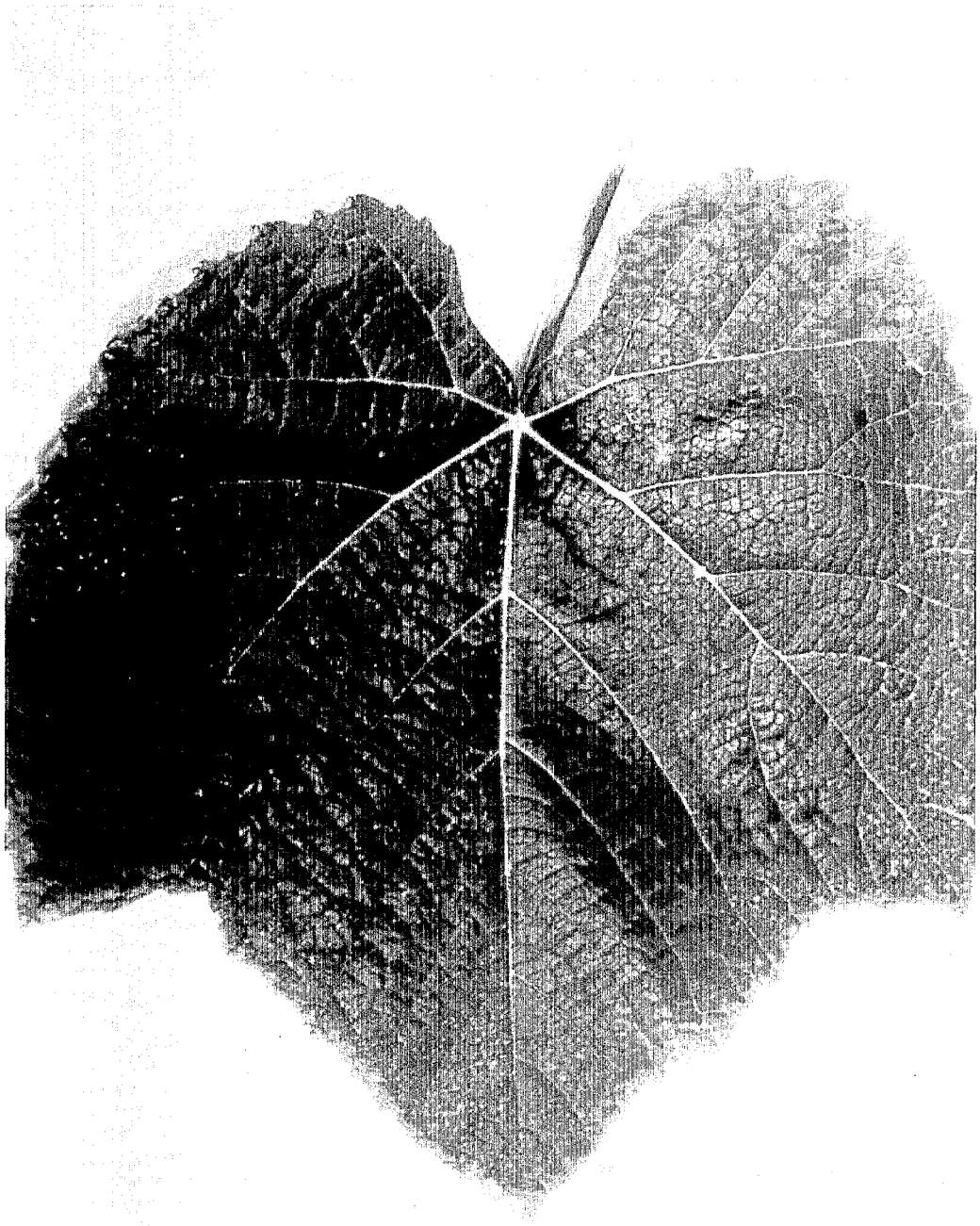

The following is a detailed description of the pomological characteristics of the subject grapevine. Color terminology is in accordance with that of the 'Royal Horticultural Society Colour Chart' published in 1966 by The Royal Horticultural Society of London, England.

Where dimensions, sizes, colors and other characteristics are given, it is to be understood that such characteristics are approximations of averages set forth as accurately as practicable.

The descriptions reported herein are from specimens grown at Clarksville, Ark., unless otherwise noted.

Attached to this application are documents from test cooperators in several states reporting performance data and attesting to the uniqueness of the new variety.

Vine:

*Size.*—Medium.

*Growth.*—Medium vigor.

*Productivity.*—Medium and consistent.

*Cold hardiness.*—Outstanding — hardy to −34° C. midwinter temperatures.

*Canes.*—Medium diameter, long, with little branching, not upright in growth habit. Diameter of mature cane: base 9 mm, midpoint 6 mm, terminal 2 mm. Internode length: base 4.6 cm, midpoint 9.5 cm, terminal 6.3 cm. Color of mature cane: base greyed orange (165-B), midpoint greyed orange (175-B), terminal greyed orange (166-B).

*Disease resistance.*—Good.

Foliage:

*Leaves.*—Color — Older leaves near base of shoots are dark green (Green Group 137B) on top surface and greyed green (194B) on lower surface. Young leaves near the tip of shoots are yellow green (144B) on upper surface and greyed green (196C) on lower surface. Petioles are yellow green (144B) on both mature and young leaves. Sinus (mature leaf at base of cane) — depth 4.75 cm, width at widest point 5.3 cm, width at midpoint 1.2 cm.

Flowers:

*Date of first bloom.*—May 11.

*Date of last bloom.*—May 20.

*Blossom color.*—Yellow green (144C).

*Shape of cluster.*—Conical, tapering, occasionally with shoulder.

*Size of cluster.*—Length: 11–20 cm, ave. 14 cm; width: 10–14 cm, ave. 11 cm; weight: 297 g, larger than Suffolk Red and Canadice; character: Well-filled but not excessively compact; number of berries: 108.

*Reproductive organs.*—Stamens — medium and erect. Pistils — medium long. Pollen — normal. Type of seedlessness — stenospermocarpy.

Fruit:

*Maturity.*—Early, with Fredonia. Average ripe dates are July 25 in Arkansas, August 24 in Ohio and September 10 in Wisconsin.

*Size of berry.*—Medium, 2.7 g ave., uniform, larger than Suffolk Red and Canadice.

*Shape.*—Spherical, uniform in shape.

*Color.*—Greyed red (182B) with bloom; greyed purple (183C) without bloom.

*Skin.*—Tender, non-adhering to flesh.

*Character of seeds.*—Stenospermocarpic seedless very small vestigial seeds present but not lignified and unnoticeable when eaten.

*Flesh.*—Melting texture.

*Flavor.*—Very sweet, with a distinct, delicate labrusca aroma and flavor. Considered outstanding.

*Soluble solids.*—23.7% (Arkansas), 27% (Texas), 17.8% (Ohio).

*Total acids.*—0.75% (Ohio).

*Eating quality.*—Excellent.

*Storage quality.*—Will store for about three months.

*Berries per cluster.*—108.

*Cluster per vine.*—48 (Ohio).

*Clusters per shoot.*—Usually two.

*Uses.*—Fresh table grape and raisins.

The Variety: The most distinctive features of the variety are its high fruit sugar content and excellent and unique flavor, its unusual cold hardiness to severe winter temperatures, and its wide climatic adaptability.

I claim:

1. A new and distinct variety of grapevine, substantially as illustrated and described, characterized by its early ripening, seedless fruit of outstanding and unique flavor, and its ability to withstand extreme cold winter temperatures.

* * * * *